United States Patent [19]

Spethmann

[11] 4,316,474

[45] Feb. 23, 1982

[54] HIGH FREQUENCY RADIATION THERAPY APPARATUS

[75] Inventor: Jens Spethmann, Lüneburg, Fed. Rep. of Germany

[73] Assignee: Firma Electric Electronic Service Jens Spethmann, Lüneburg, Fed. Rep. of Germany

[21] Appl. No.: 148,175

[22] Filed: May 8, 1980

[30] Foreign Application Priority Data

Aug. 17, 1979 [DE] Fed. Rep. of Germany ... 7923476[U]

[51] Int. Cl.$^3$ ............................................... A61B 5/00
[52] U.S. Cl. .............................. 128/804; 219/10.55 F
[58] Field of Search ............... 128/804, 783, 784, 788, 128/799, 802; 219/10.55 R, 10.55 A, 10.55 F

[56] References Cited

U.S. PATENT DOCUMENTS

| | | | |
|---|---|---|---|
| 2,407,690 | 9/1946 | Southworth | 128/804 |
| 3,230,957 | 1/1966 | Seifert | 128/804 |
| 3,783,221 | 1/1974 | Soulier | 219/10.55 A |

FOREIGN PATENT DOCUMENTS

| | | | |
|---|---|---|---|
| 2701934 | 7/1978 | Fed. Rep. of Germany | 128/804 |
| 52-20039 | 2/1977 | Japan | 219/10.55 R |
| 1188490 | 4/1970 | United Kingdom | 128/804 |

*Primary Examiner*—Lee S. Cohen
*Attorney, Agent, or Firm*—Toren, McGeady & Stanger

[57] ABSTRACT

The invention relates to a high frequency radiation therapy apparatus permitting therapy on the lying patient and which is constructed in such a way that a high frequency generator with a waveguide is displaced in the vicinity of the lying surface of a patient on a couch. The waveguide used is subdivided into a plurality of separately operable groups to obtain a lateral power distribution. Each group has slot-like openings in the wall current area of the waveguide and the openings of each group can be closed independently of one another.

9 Claims, 4 Drawing Figures

HIGH FREQUENCY RADIATION THERAPY APPARATUS

BACKGROUND OF THE INVENTION

The most varied constructions of high frequency therapy apparatus are known. It is common to all the said apparatus that they generate a high frequency field by means of suitable transmitters and said field penetrates the patient's body and brings about an endogenous thermal action therein. Due to limited resorption in the adipose tissue and at the same time a good energy conversion in the perfused tissue microwave therapy has become more widely used than the previously preferred short wave equipment.

However, when using microwave equipment the power limit is very rapidly reached, because there is a natural limit of the power rise in the excellently resorbing skin layer. An increase in the apparatus power can admittedly be attained by larger electrodes. However, this only has an effect on large treatment surfaces. In order to increase the penetration depth, the radiation energy per $cm^2$ must be increased, but the aforementioned strong resorption in the skin layer is prejudicial to this.

The previously preferred short waves used in such therapy apparatus have been supplemented by microwaves and ultra-high frequency wave equipment. The individual therapy forms differ only in their electrode application and only then to an insignificant extent. In each case, there is a movable sheet steel casing, where the radiation source electrode is carried on one or, in the case of short wave, generally two supporting arms. The radiation source is generally connected to the apparatus by a high frequency cable. The known high frequency therapy apparatus require a large amount of space due to the arranging and directing of the radiation source and the supporting arm or arms.

It has been found that it is in connection with the accessories such as radiation source arms, high frequency cables, etc. that the main problems linked with expensive repairs are encountered.

With the known high frequency therapy apparatus, it is impossible to avoid scorched connecting cables and sockets, damaged radiation sources and loose or broken-off supporting arm joints. In addition, the swivel hinge connected to the hinged bracket for the radiation source used on known high frequency therapy apparatus is difficult of access, access being necessary so that the radiation source can be kept in the particular desired position. To adjust the radiation source, the latter is often used as a lever arm, but this can in turn damage the radiation source. Furthermore, considerable forces are required for swinging the radiation source, unless mechanical or electromotive auxiliary pivoting means are used, which considerably increases the cost of such high frequency therapy apparatus. It is also impossible with the known high frequency therapy apparatus to house the magnetron, i.e. the high frequency generator in the radiation source, because otherwise the weight of the radiation source at the free end of the hinged bracket would be even greater, so that single swivel hinges would be inadequate.

BRIEF SUMMARY OF THE INVENTION

The problem of the present invention is to provide a high frequency radiation therapy apparatus which can be operated extremely easily and rationally, which has no fault-prone components and which by adjusting to different treatment areas is suitable for use both on the entire body and for individual parts of the body.

According to the invention, this problem is solved by a high frequency radiation therapy apparatus, wherein it comprises the combination of the following features:

(a) in a couch frame of a couch with a lying surface a slide is arranged so as to be movable in the longitudinal direction of the couch beneath the lying surface and which carries a high frequency generator with a waveguide and a control section;

(b) the waveguide having a box-like casing has a length approximately corresponding to the width of the lying surface and in order to obtain a lateral power distribution is subdivided into two or more, separately operable groups of slot-shaped openings formed in the front panel of the casing and in the wall current area of the waveguide;

(c) the slot-shaped openings of each group can be closed independently of one another by means of closing devices using knobs on the control section.

A high frequency radiation therapy apparatus constructed in this way permits therapy to be carried out on lying patients, which permits the treatment of patients who cannot assume a sitting or standing position. Furthermore, the therapy apparatus constructed in couch-like manner permits space-saving in the generally constricted treatment cubicles. As the radiation source or waveguide is displaceable in the longitudinal direction of the couch, below the lying surface of the therapy apparatus it is possible to reach any part of the patient's body which is to be treated. The wave-guide can be moved up to any part of the body without exerting any noteworthy force.

This therapy apparatus also has no fault-prone components, because the high frequency generator and the waveguide, together with the associated electrical components and control mechanism are housed in the slide displaceable below the lying surface and which is constructed in a casing-like manner. This obviates high frequency cables, plug connections and the pivotable supporting arm otherwise used in the known apparatus for supporting the radiation source. In addition, the couch-like therapy apparatus requires no additional space in practice rooms or surgeries, because the latter in any case contain couches for treatment purposes, for taking electrocardiograms, for resting, etc. Thus, the therapy apparatus can be used in place of the couches otherwise employed in the surgeries.

As a result of the lying treatment position made possible by the therapy apparatus particularly favourable static conditions are obtained, because with a sitting patient muscular stresses are an undesired attendant phenomenon. Unlike in the case of a sitting patient, when using the therapy apparatus it is possible to maintain the position assumed through the radiation period. This applies for example to lumbago treatment. A painless position can easily be found and therefore maintained.

Due to the fact that the waveguide is constructed in such a way that different treatment fields can be set and applied at any point in the longitudinal direction of the couch, the possibility is provided by switching in or off individual treatment fields to treat the right, central or left parts of a patient's body. The proven high frequency pulse therapy ensures a maximum penetration depth and therefore optimum endogenous heating with minimum surface loading.

According to the invention, the waveguide is developed in such a way that on the high frequency radiation input side the waveguide has two slot-shaped openings combined into a group, followed by three slot-shaped openings, combined into a group and then four slot-shaped openings combined into a group in the front panel, the slot-shaped openings of each group being closable by means of a closing device constructed as a slide plate and which is provided with a number of equally large openings which corresponds to the number of slot-shaped openings in the waveguide casing and are spaced from one another in such a way that each is somewhat larger than the width of each slot-shaped opening in the waveguide casing.

Due to this advantageous construction of the waveguide, the possibility is provided on one side of switching on, off or in different treatment fields and on the other side it is ensured by freeing all the slot-shaped openings in the waveguide casing that equal radiation intensities are achieved in all sections of the waveguide.

Further advantageous developments of the invention can be gathered from the subclaims.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
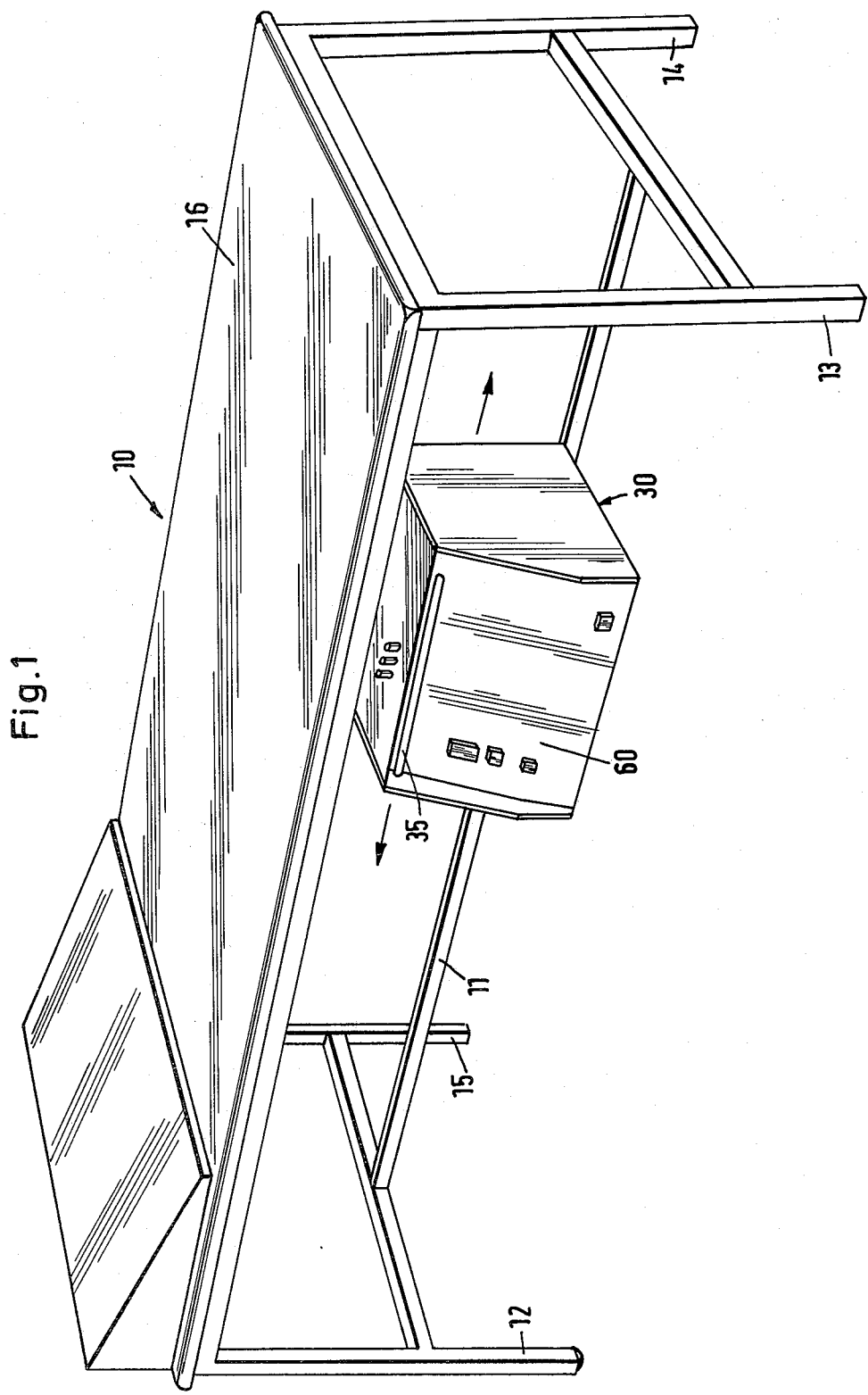
FIG. 1 a high frequency radiation therapy apparatus constructed as a couch with a slide movable beneath the lying surface and with a high frequency generator and waveguide located therein, in a diagrammatic view.

The high frequency radiation therapy apparatus comprises a couch 10, its couch frame 11 and the frame legs 12, 13, 14, 15. The couch frame 11 has a preferably cushioned lying surface 16, which can also comprise a number of parts (FIG. 1).

Figure 2:
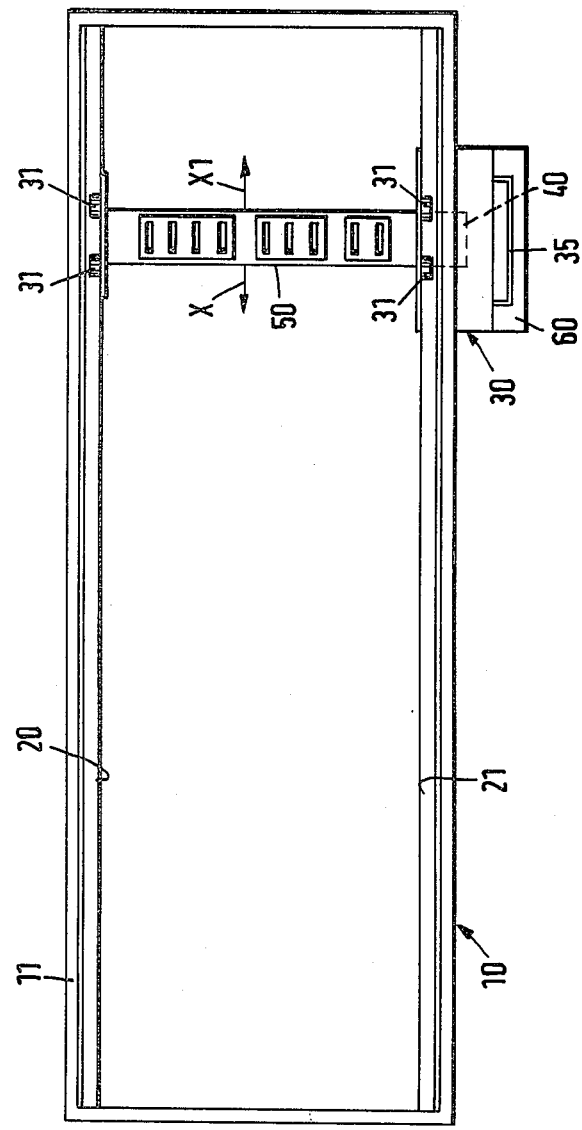
FIG. 2 the high frequency radiation therapy apparatus with the lying surface removed in a view from above onto the couch frame.

Below lying surface 16, couch frame 11 has parallel, spaced guide rails 20, 21 running in the longitudinal direction of the couch along which is displaceable a slide 30 or along which can be moved the couch 30 by means of runners 31 provided thereon (FIG. 2).

The slide 30 is constructed in box-like manner and receives a high frequency generator 40, a waveguide 50 and a control section 60. The high frequency generator 40 with waveguide 50 and control section 60 are displaceable in the direction of arrow X1 with the slide 30. The two guide rails 20, 21 can be replaced by a single, centrally arranged guide rail, which then receives the slide 30. For this purpose, the guide rail is provided with a cross-sectional profile, whilst the slide 30 has a corresponding mating profile, so that the slide 30 is guided and held in the said guide rail.

Control section 60 has the necessary electric components, time switches, knobs, etc. for operating the therapy apparatus. A handle indicated on slide 30 at 35 in FIGS. 1 and 2 is used for the effortless movement of slide 30 below the lying surface 16. In the embodiment shown in FIGS. 1 and 2, the slide 30 has a length corresponding to the width of couch 10, part of the slide being formed by waveguide 50.

Waveguide 50 arranged in slide 30 comprises a box-like casing 51 made from metallic materials, whose front panel 52 facing the lying surface 16 has a plurality of slot-shaped openings 70, 71, 80, 81, 82, 90, 91, 92 and 93. These slot-shaped openings are at right angles to the longitudinal direction of the waveguide casing 51. The high frequency rays from the high frequency generator 40 enter in the direction of arrow Y.

Figure 3:
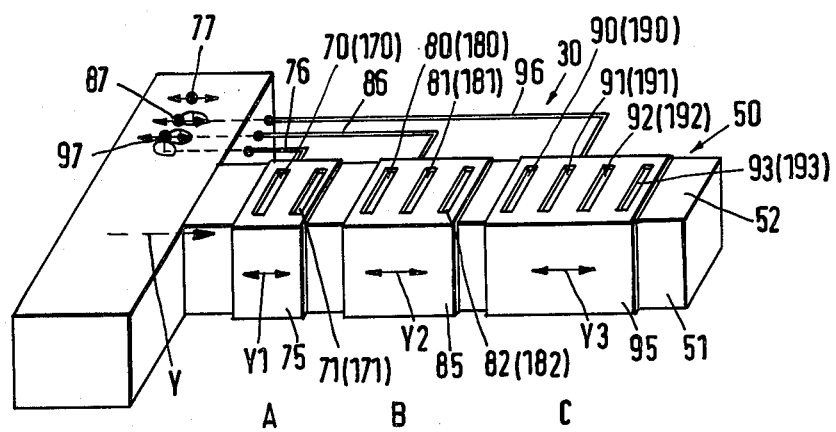
FIG. 3 a diagrammatic view of the therapy apparatus waveguide.
Figure 4:
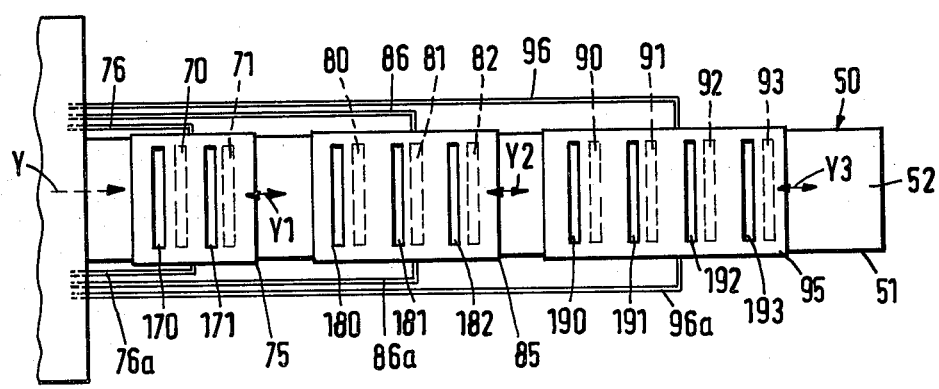
FIG. 4 the waveguide in a view from above.

In order to achieve a lateral power distribution the entire width or length of waveguide 50 is divided into three separate and separable groups A, B and C, each of which has a plurality of slot-shaped openings. Group A has two slot-shaped openings 70, 71, group B three openings 80, 81, 82 and group C four openings, 90, 91, 92 and 93. Group A with two slot-shaped openings 70, 71 is provided in the waveguide casing 51 on the high frequency radiation input side. Groups B and C with the slot-shaped openings 80 to 82 and 90 to 93 are at the other end of waveguide casing 51. The different number of slot-shaped openings in the three groups A, B and C permits a uniform power distribution if all the openings of groups A, B and C are open. The slot-shaped openings 70, 71, 80 to 82 and 90 to 93 are all of the same size and shape (FIGS. 3 and 4).

The slot-shaped openings 70, 71, 80 to 82 and 90 to 93 of each of the groups A, B and C are closable by means of slide plates 75, 85, 95. The slide plates can be U-shaped or can embrace the waveguide casing 51 in an annular manner. It is important that the plates 75, 85, 95 can be displaced on the waveguide casing 51 and specifically in the longitudinal direction thereof. It is obviously necessary for there to be a good contact between the metallic slide plates 75, 85, 95 and the box-shaped waveguide casing 51.

Each of the slide plates 75, 85, 95 is provided with a plurality of slot-shaped openings in accordance with its association with the individual groups A, B and C and this corresponds to the plurality of slot-shaped openings 70, 71, 80 to 82 and 90 to 93 in groups A, B and C. Thus, slide plate 75 has two slots 170, 171 for the slot-shaped openings 70, 71 of group A, whilst slide plate 85 has three slots 180, 181, 182 for the slot-shaped openings 80 to 82 of group B and slide plate 95 has four slots 190, 191, 192, 193 corresponding to the four slot-shaped openings 90 to 93 of group C. The shape and size of slots 170, 171, 180 to 182 and 190 to 193 correspond to the slot-shaped openings 70, 71, 80 to 82 and 90 to 93, so that when slide plates 75, 85 and 95 are in an appropriate position slots 170, 171, 180 to 182 and 190 to 193 coincide with the slot-shaped openings 70, 71, 80 to 82 and 90 to 93 in waveguide casing 51 (FIG. 3).

The reciprocal spacing of slots 170, 171, 180 to 182 and 190 to 193 approximately corresponds to the width of the slot-shaped openings 70, 71, 80 to 82 and 90 to 93, so that on displacing the slide plates 75, 85, 95 in the direction of arrows Y1, Y2, Y3 the slot-shaped openings of the individual groups A, B and C are closed or, if desired, can be opened again. This provides the possibility of setting seven different treatment fields, which in the longitudinal direction of couch 10 can be applied to any pint. Irradiation takes place from below through the cushions of lying surface 16 of couch 10.

In order to operate the slide plates 75, 85 95 each of them is connected to an operating rod 76, 86, 96. The free ends of these operating rods 76, 86, 96 are guided into the control section 60 and carry knobs 77, 87, 97, so that from control section 60 it is possible to bring about the closing or opening of the slot-shaped openings 70, 71 and/or 80 to 82 and/or 90 to 93 by corresponding displacement of slide plates 85, 75, 95. However, other operating mechanisms can also be provided with slide plates 75, 85, 95. The important point is that the displacement of the slide plates can take place in a completely satisfactory manner. Thus, it is possible to displace each individual slide plate 75 or 85 or 95 with two operating rods positioned laterally of the slide plate and the waveguide casing 51, whose free ends located in control section 60 are interconnected and in this case the said connecting portions carry the knobs 77, 87 or 97 (FIG. 4).

In this embodiment, shown in FIG. 4, the slide plates 75 or 85 or 95 are operated by the connected operating rods 76, 76a or 86, 86a or 96, 96a.

Other closing means can be used in place of slide plates 75 or 85 or 95.

There can be a random number of slot-shaped openings in waveguide casing 51. There can also be a random number of slot-shaped openings combined into the individual groups, but the arrangement of the slot-shaped openings must be such that if all the said openings in waveguide casing 51 are open, the rays can pass out of them with the same intensity and this can also be achieved in that the slot-shaped openings in wave-guide casing 51 are given different dimensions.

What is claimed is:

1. High frequency radiation therapy apparatus comprising: a couch defining a generally horizontal surface upon which a patient may lie in the prone position; a slide assembly slidably mounted on said couch immediately beneath said surface so as to be movable in the longitudinal direction thereof; high frequency generator means mounted in said slide assembly and movable therewith relative to said couch surface; wave guide means mounted as part of said slide assembly through which high frequency radiation from said generator means is delivered from beneath said surface to a patient lying thereon; said wave guide means comprising a hollow wave guide housing extending lengthwise laterally beneath said surface and having a length at least approximatey equivalent to the width of said surface, a plurality of slotted openings formed in the top of said wave guide housing facing upwardly toward the underside of said horizontal surface, said slotted openings being arranged in a plurality of groups and distributed across the width of said surface and means for selectively closing the slotted openings of each group independently of the openings of another group to block passage of radiation therethrough.

2. Apparatus according to claim 1 wherein the number of slotted openings in each of said groups increases progressively laterally of said surface from one side thereof to the other.

3. Apparatus according to claim 1 wherein each of said slotted openings has a generally rectangular configuration with a length dimension extending longitudinally of said horizontal surface.

4. Apparatus according to claim 3 wherein each of said slotted openings is spaced from each adjacent opening by a distance greater than the width of said slotted openings.

5. Apparatus according to claim 1 wherein said high frequency generator means is located at one end of said hollow wave guide housing and operates to emit radiation therethrough in a direction laterally of said horizontal surface from one side thereof to another, and wherein the number of slotted openings in each of said groups increases progressively across said surface in the direction of said emitted radiation.

6. Apparatus according to claim 4 wherein said groups of slotted openings comprise a first group having two slotted openings, a second group having three slotted openings, and a third group having four slotted openings, said first group being closest to said generator means and said third group being furthest therefrom.

7. Apparatus according to claim 1 wherein said means for closing said slotted openings comprise a plurality of slide plates movable relative to said wave guide housing, with one slide plate being provided for each of said groups of slotted openings, each of said slide plates being formed with slotted openings which correspond in number and configuration to the slotted openings of a respective group in said wave guide housing.

8. Apparatus according to claim 7 including means for moving said slide plates independently of each other relative to said wave guide housing.

9. Apparatus according to claim 1 wherein each of said slotted openings are identically dimensioned.

* * * * *